United States Patent [19]

Beck

[11] Patent Number: 5,727,562

[45] Date of Patent: Mar. 17, 1998

[54] PNEUMATICALLY SENSED RESPIRATION MONITOR & METHOD

[76] Inventor: Gregory S. Beck, 8230 E. Alpine Ct., Anaheim, Calif. 92808

[21] Appl. No.: 679,260

[22] Filed: Jul. 11, 1996

[51] Int. Cl.[6] ............................................. A61B 5/08
[52] U.S. Cl. ........................... 128/721; 128/716; 128/720; 128/725
[58] Field of Search ........................... 128/716, 720, 128/721, 725

[56] References Cited

U.S. PATENT DOCUMENTS

| | | |
|---|---|---|
| 1,619,886 | 3/1927 | Ryan . |
| 2,194,809 | 3/1940 | Powell, Jr. . |
| 2,233,506 | 3/1941 | Azaretti . |
| 3,081,765 | 3/1963 | Kompellien . |
| 3,097,639 | 7/1963 | Streimer . |
| 3,268,845 | 8/1966 | Whitmore . |
| 3,547,106 | 12/1970 | Bornmann . |
| 3,658,052 | 4/1972 | Alter . |
| 3,782,368 | 1/1974 | Reibold ........................ 128/721 X |
| 3,831,586 | 8/1974 | Petit . |
| 3,836,900 | 9/1974 | Mansfield . |
| 3,882,847 | 5/1975 | Jacobs . |
| 3,993,994 | 11/1976 | Goggins . |
| 4,146,885 | 3/1979 | Lawson, Jr. ..................... 128/721 |
| 4,169,462 | 10/1979 | Strube . |
| 4,296,757 | 10/1981 | Taylor ........................... 128/721 |
| 4,602,643 | 7/1986 | Dirtz ............................ 128/721 |
| 4,838,279 | 6/1989 | Fore ............................. 128/721 |
| 4,862,144 | 8/1989 | Tao . |
| 4,895,102 | 1/1990 | Dolliver ........................ 128/721 |
| 5,074,299 | 12/1991 | Dietz . |
| 5,088,501 | 2/1992 | Niwisch ......................... 128/721 |
| 5,107,855 | 4/1992 | Harrington et al. ............... 128/721 |
| 5,277,194 | 1/1994 | Hosterman . |
| 5,295,490 | 3/1994 | Dodakian ........................ 128/721 |
| 5,400,012 | 3/1995 | Walton . |
| 5,540,733 | 7/1996 | Testerman et al. ................ 128/721 X |

*Primary Examiner*—Jennifer Bahr
*Assistant Examiner*—Stephon Huang
*Attorney, Agent, or Firm*—John J. Connors; Connors & Assoc.

[57] ABSTRACT

A respiration monitor includes a sensing element having a pressure chamber filled with gas. The sensing element is adapted to be placed in contact with a breathing subject, with the pressure in the chamber increasing as the subject inhales and decreasing as the subject exhales. A pressure switch in communication with the pressure chamber opens as the subject exhales and closes as the subject inhales to control the operation of a timing circuit. The timing circuit includes an audio alarm mechanism activated when the switch is not closed within a predetermined threshold period. The chamber has at least one gas port which places the chamber in communication with ambient air pressure, so that within a pressure equalization time interval the pressure within the chamber equalizes to that of ambient air pressure and the switch is opened. This port is sized so that the pressure equalization time interval is longer than the normal cycle of inhalation and exhalation of the subject but shorter than the predetermined threshold period. The size, or number openings, comprising the port is sufficiently restrictive so that changes in pressure within the gas chamber are detected, causing the switch to operate to open or close as required.

14 Claims, 4 Drawing Sheets

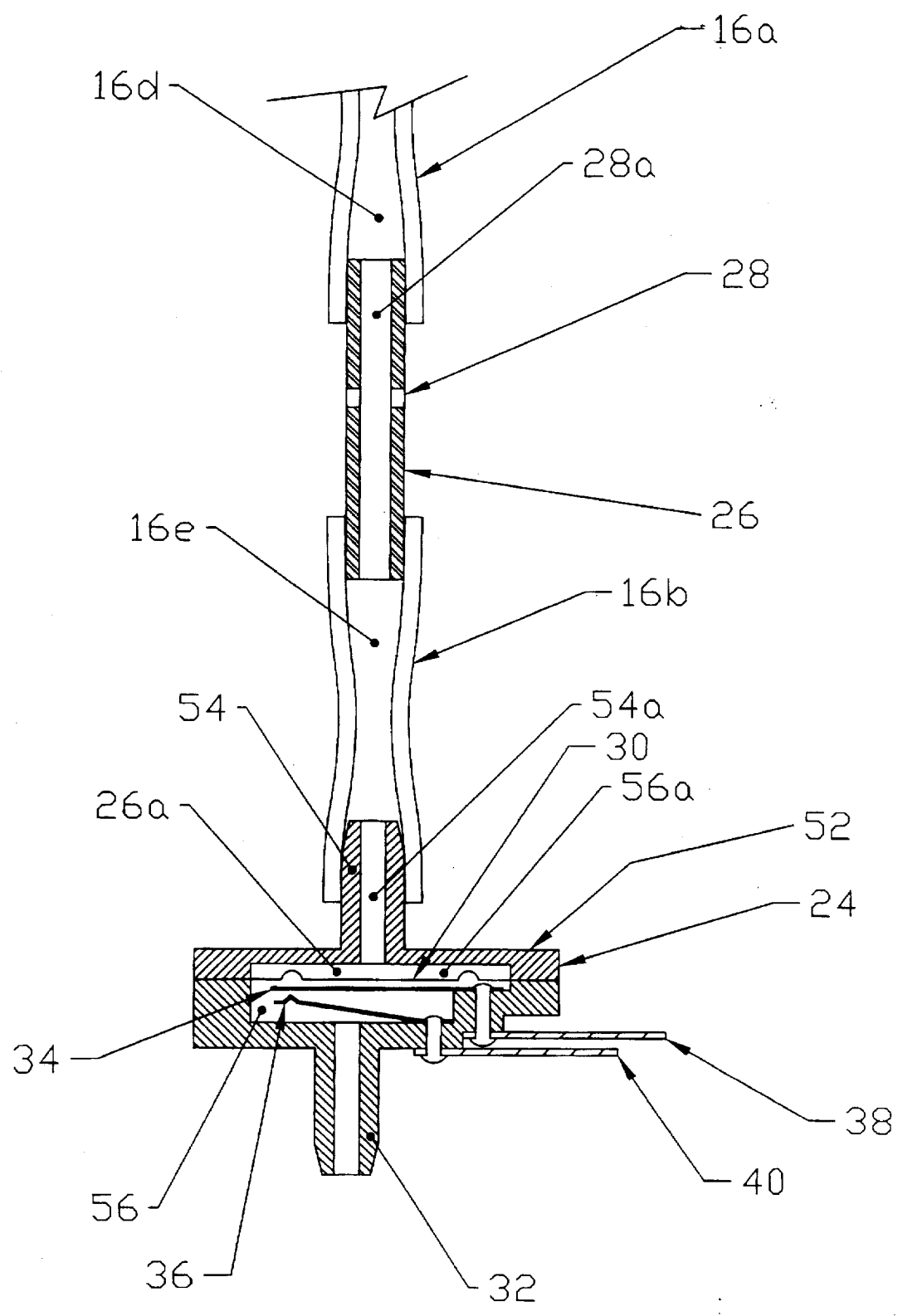

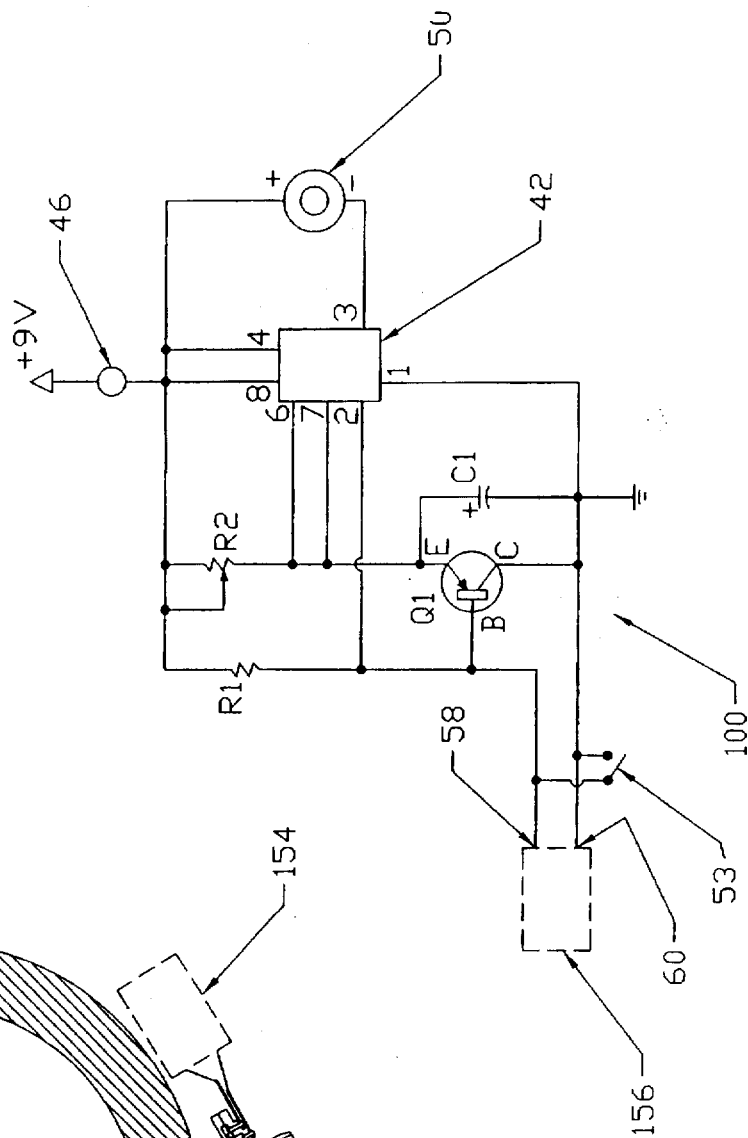
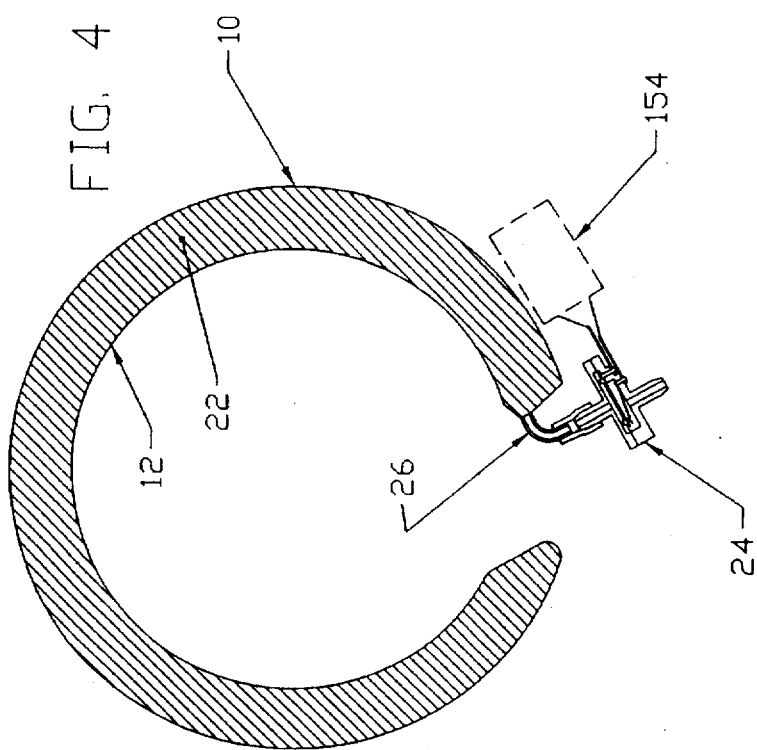

PNEUMATICALLY SENSED RESPIRATION MONITOR & METHOD

BACKGROUND OF THE INVENTION

FIELD OF THE INVENTION

This invention relates to electro-pneumatic human motion detection devices and methods often used to signal the onset of apnea in adults or infants.

BACKGROUND DISCUSSION

Sudden Infant Death Syndrome (SIDS) is one of the leading causes of death in infants between the ages of two weeks and one year. Until the causes of SIDS are identified and a solution developed, parents and physicians alike have only one choice in avoiding SIDS: monitoring the infant during sleep periods to detect the onset of apnea.

In an attempt to lessen the burden of monitoring a sleeping infant throughout their sleep periods, various devices have been developed which monitor an infant's breathing pattern and warn of a change in the breathing pattern. These devices have been difficult to apply and set up, are unreliable, are unable to compensate for an infant's other movements, such as rolling during sleep, or are too expensive for practical application in the parent's homes.

SUMMARY OF THE INVENTION

It is the objective of this invention to provide a reliable, low cost respiration monitor for detecting the onset of apnea in a breathing subject, particularly infants.

This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include reliability, low cost, and avoidance of false alarms.

The first feature of the respiration monitor of this invention is that it includes a sensing element including a pressure chamber filled with gas. The sensing element is adapted to be placed in contact with the subject, so that the pressure in the chamber increases as the subject inhales and decreases as the subject exhales. This sensing element may be a belt wrapped about the chest of the subject or a mat on which the subject lies while sleeping. It typically is a balloon-like structure with walls made of an elastomeric material which is resilient. When the subject inhales, the volume of the chamber decreases slightly, increasing slightly the pressure of the gas in the chamber. When the subject exhales, the chamber returns to its original volume due to the resilient nature of the elastomeric material.

The second feature is a pressure switch in communication with the pressure chamber. This switch is activated as the subject breathes. For example, as the subject exhales the switch is opened and as the subject inhales the switch is closed. A reverse arrangement could also be established, so that exhaling closes the switch and inhaling opens the switch. The important consideration is that the switch is activated to change from a first state to a second state as the subject exhales and to change from the second state to the first state as the subject inhales. The pressure switch preferably is a differential pressure switch, with a first side in communication with the gas chamber and a second side in communication with ambient pressure.

The pressure chamber includes the volume of gas in the sensing element in contact with the subject, the volume of gas in any tube connecting the sensing element to the switch, and the volume of gas in first side of the switch in communication with the tube and sensing element. Only the volume of the sensing element changes as the subject breathes. If this volume in the sensing element is low relative to the volume of gas in the tube and the volume of gas in first side of the switch, the switch may not be sensitive enough to detect small changes in pressure resulting from the motion of the subject due to breathing. In other words, changes in volume in the sensing element relative to the total volume of gas in the chamber produces a change in pressure which the switch cannot detect. Typically, the total volume of the chamber ranges between 5 and 9 cubic inches for applications to detect apnea in infants. In this case, if the volume of the sensing element comprises more than ninety percent (90%) of the total volume of the chamber, and the volume of the first side of the switch is less than three percent (3%) of the total volume of the chamber, the switch will be sensitive enough and be activated as the subject breathes.

The third feature is a timing circuit connected to the switch and including an audio alarm mechanism. The timing circuit activates the alarm mechanism when the switch is not activated within a predetermined threshold period. The alarm indicates that the monitor of this invention is not operational or that the subject has stopped moving. The timing circuit may include a manually operated reset switch that resets the timing circuit after an alarm occurs.

The fourth feature, which prevents false alarms, calls for the chamber to have at least one gas port which places the chamber in communication with ambient air pressure, so that within a pressure equalization time interval the pressure within the chamber equalizes to that of ambient air pressure and the switch is activated, that is opened or closed depending on the design of the timing circuit. This feature enables the monitor to be used at different altitudes and as the air pressure changes with changing weather conditions. This port, which may be one large opening or several small openings, is sized so that the pressure equalization time interval is longer than the normal cycle of inhalation and exhalation of the subject but shorter than the predetermined threshold period established by the timing circuit. Consequently, if the subject, for example rolls to create an abrupt and abnormal increase or decrease in the pressure in the chamber, the pressure within the chamber has sufficient time to return to a normal condition before the alarm is activated. Typically, the pressure equalization time interval is greater than 5 seconds and the predetermined threshold period is less than 25 seconds. The hole size, or number of holes, must be sufficiently restrictive to insure that the pressure change produced by the change in volume of the sensing element still is detected by the pressure switch. If the size, or number of holes, causes gas to leak out of, or into, the gas chamber too rapidly, typically, within less than one second, the switch may not detect any pressure change.

The fifth feature is that the timing circuit may include a transmitter that is activated and deactivated by the closing or opening of the switch as discussed above. A receiver in communication with the transmitter and responsive to the activation and deactivation of the transmitter turns on the alarm mechanism when the switch fails to change from the second to the first state within the predetermined threshold period. Alternately, if the switch fails to change from the second to the first state within the predetermined threshold period, only then is the transmitter activated to transmit to the receiver a signal which produces the alarm.

This invention also includes a method for detecting the onset of apnea in a breathing subject. This method includes the following steps:

(a) placing the subject in contact with a sensing element having a pressure chamber filled with gas, said sensing element being adapted to be placed in contact with a breathing subject, with the pressure in the chamber increasing as the subject inhales and decreasing as the subject exhales, (b) placing a differential pressure switch in communication with the pressure chamber, said switch changing from a first state to a second state as the subject exhales and changing from the second state to the first state as the subject inhales, and (c) connecting to the switch a timing circuit including an alarm mechanism, said timing circuit activating the alarm mechanism when the switch fails to change from a second state to a first state within a predetermined threshold period, (d) said chamber having at least one gas port which places the chamber in communication with ambient air pressure, so that within a pressure equalization time interval the pressure within the chamber equalizes to that of ambient air pressure and the switch changes from the second state to the first state, said port being sized so that said pressure equalization time interval is longer than the normal cycle of inhalation and exhalation of the subject but shorter than said predetermined threshold period and being sufficiently restrictive so that changes in pressure within the gas chamber are detected to cause the switch to change states.

DESCRIPTION OF THE DRAWING

The preferred embodiments of this invention, illustrating all its features, will now be discussed in detail. These embodiments depict the novel and non-obvious monitor and method of this invention as shown in the accompanying drawing, which is for illustrative purposes only. This drawing includes the following figures (Figures), with like numerals indicating like parts:

FIG. 3 is an enlarged cross-sectional view of the differential pressure switch employed in this invention.

FIG. 4 is a plan view of the sensing component in a portable embodiment of the sensing belt portion of this invention.

FIG. 5 is a schematic diagram showing the principle electronic components contained within the warning component of the embodiment of this invention shown in FIG. 4.

DETAILED DESCRIPTION OF THE PREFERRED EMBODIMENTS

Figure 1:
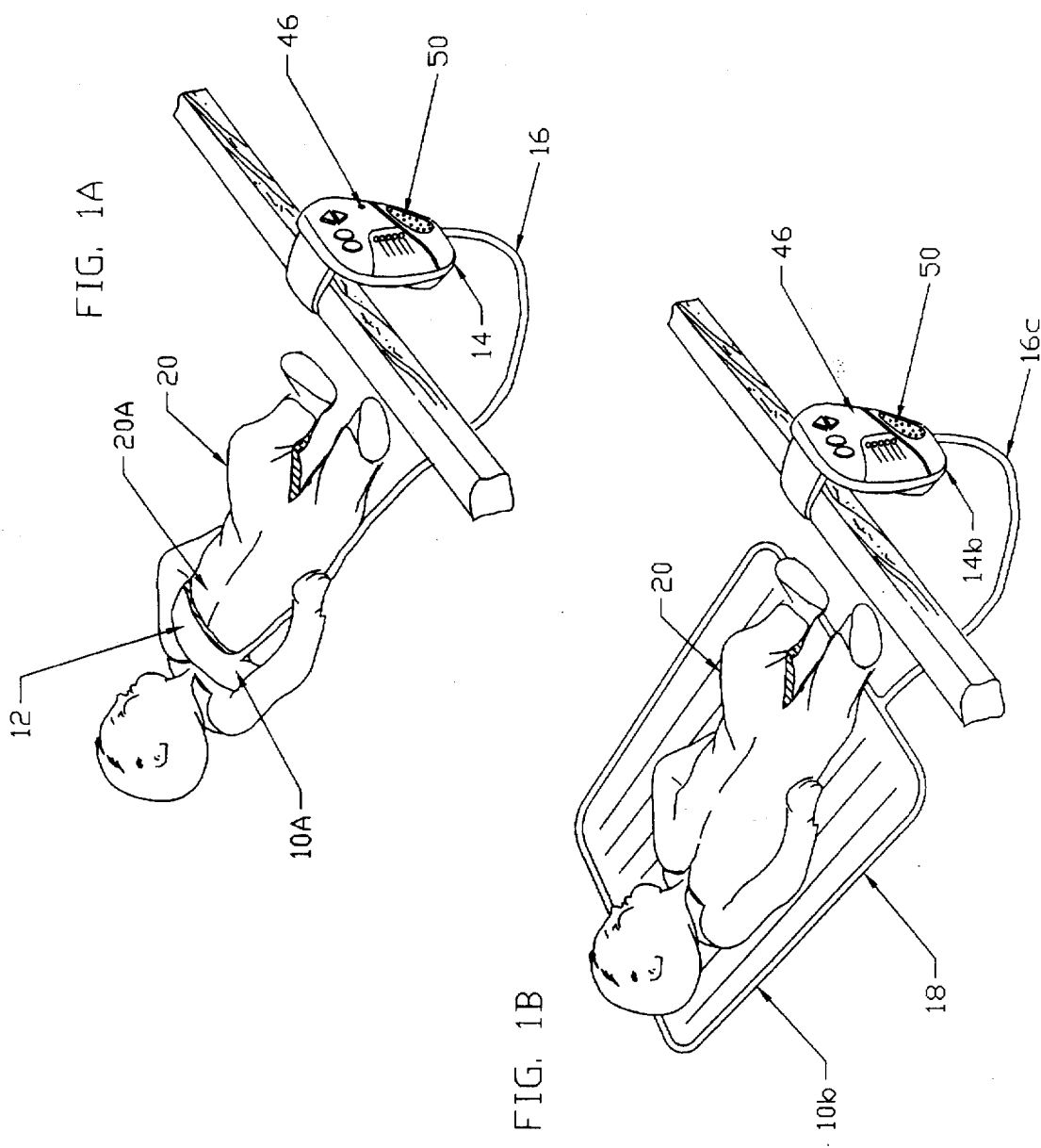
FIG. 1A is a perspective view showing a sensing belt embodiment of the monitor of this invention.
FIG. 1B is a perspective view showing a sensing embodiment of the monitor of this invention.
Figure 2:
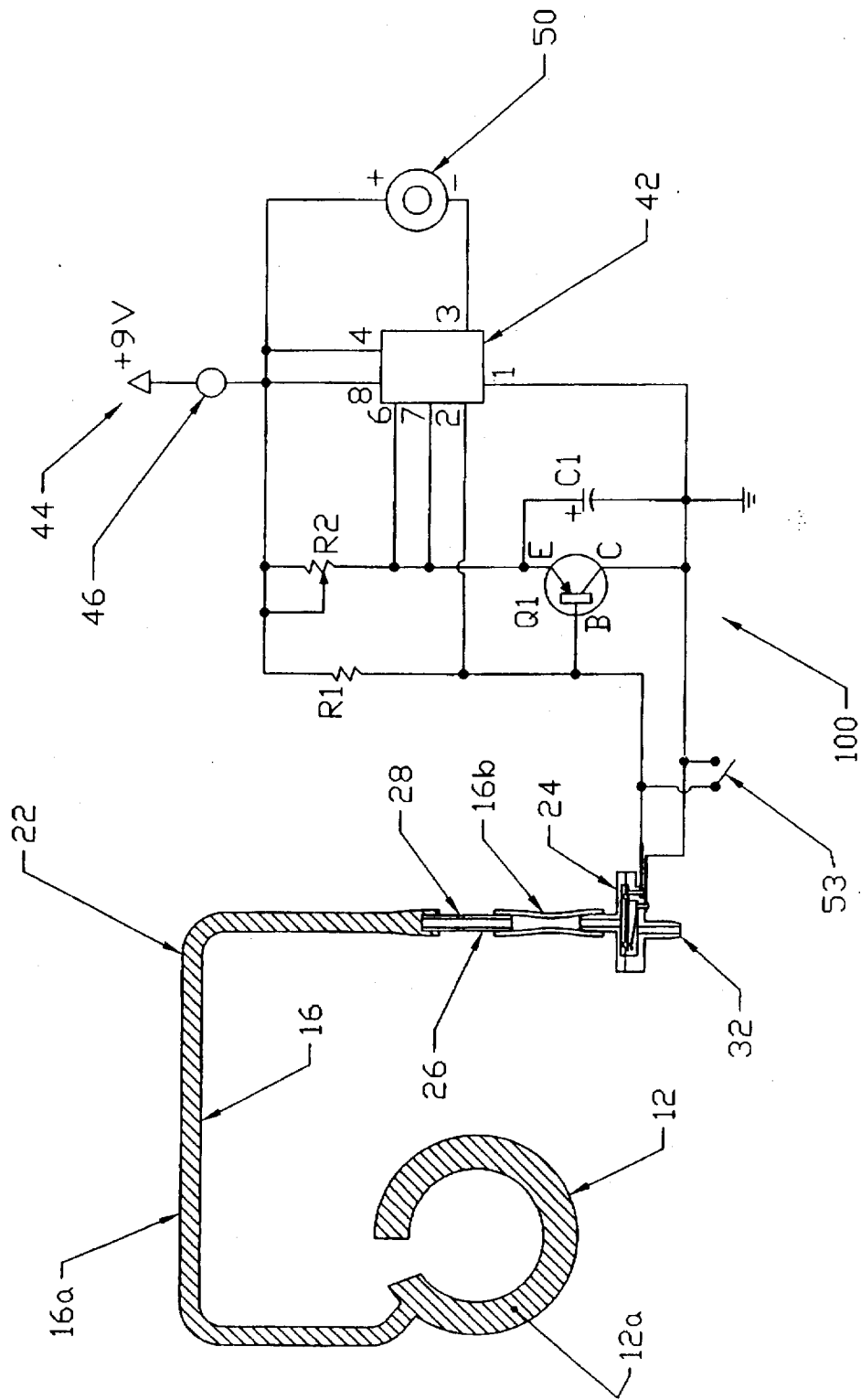
FIG. 2 is a schematic diagram showing the principal pneumatic and electronic components contained within the monitor shown in FIGS. 1A and 1B.

As depicted in FIG. 1A, the respiration monitor 10a of this invention includes a belt 12 to detect the breathing of an infant 20, a differential pressure switch 24 (FIG.2), a flexible tube 16 which pneumatically connects the belt to the switch, and a timing circuit 100 (FIG. 2), which includes an audio alarm 50. The sensing belt 12 is worn around the chest 20a of the infant 20 being monitored. As best illustrated in FIG. 3, an orifice adapter 26 (FIGS. 2 and 3) connects one section 16a of the tube 16 to the differential pressure switch 24 through another section 16b of the tube 16. A monitor enclosure 14 houses the switch 24 and timing circuit 100.

As shown in FIG. 1B, an alternate embodiment of this invention, respiration monitor 10b, utilizes a sensing mat 18 instead of the sensing belt 12 to detect inhalation and exhalation. The sensing mat 18 is removably attached by a flexible tube 16c to a monitor enclosure 14b, which contains the differential pressure switch 24 and the timing circuit 100. The respiration monitor 10b functions in essentially the same way as the respiration monitor 10a, except the infant lies on the mat, which has a volume of air that is compressed as the infant inhales and expands as the infant exhales.

The pressure switch 24 is a standard component which may be purchased from Micro Pneumatic Logic, of Fort Lauderdale, Fla., and is identified as MPL 503. As best illustrated in FIG. 3, the switch 24 includes a housing 52 having ports 32 and 54 in communication with opposite sides of a cavity 56 in the housing. A flexible diaphragm 30 is seated between the ports 32 and 54. Between the diaphragm 30 and the port 32 are a pair of electrical contacts 34 and 36, which are electrically connected to the timing circuit 100. Contact 36 is stationary and contact 34 is a moveably spring element, flexing towards the contact 36 when the pressure in the interior 12a of the belt 12 causes the diaphragm 30 to move and returning to its nonflex condition when the diaphragm 30 returns to its normal condition shown in solid lines in FIG. 3.

The sensing belt 12 (and mat 18) is made of a elastomeric material such as, for example, silicone, which is resilient. The belt 12 has a thin, flexible wall defining a hollow interior 12a. Since both the sensing mat 18 and the sensing belt 12 are constructed of resilient material, they return to their original volume upon exhaling. The flexible tube 16 has a hollow interior 16d and the orifice adapter 26 has a hollow interior 28a. When the belt 12, tube sections 16a and 16b, and adapter 26, are connected to the switch 24, a gas chamber 22 is formed including the hollow interiors 12a, 16d and 16e, and 28a, respectively, of the belt, tube sections 16a And 16b and adapter 26, and the space 56a between the diaphragm 30 and the port 54, including the space 54a of the port 54. The total volume of the gas chamber is, therefore, the combined volumes of the belt 12, the tube sections 16a and 16b, the adapter 26, and the switch 24.

The combined volume of the spaces 54a and 56a, respectively, of the port 54 and cavity 56, and the hollow interiors 16d and 16e, and 28a, respectively, of the tube sections 16a and 16b, and adapter 26, is relatively small, typically in combination less than 0.2 cubic inches, normally ranging between 0.1 and 0.3 cubic inches. This is a volume of less than 3 percent of the total volume which is about 8 cubic inches. Because the volume of gas outside the interior 12a of sensing belt 12 is so small, a small volume increase or decrease within sensing belt causes a relatively large deflection in the diaphragm 30 either towards the moveable contact 34 during inhalation or away from the contact 34 during exhalation. When the infant 20 inhales, the expansion of her or his chest decreases the volume of the gas in the interior 12a of the belt 12, increasing the pressure in the gas chamber 22 which is detected by the switch 24. This increase in the pressure of the gas chamber 22 causes the diaphragm 30 to flex and push the contact 34 into engagement with the contact 36, closing the pressure switch 24.

It is desirable to prevent false alarms caused by movements of the infant 20 such as rolling, which may abruptly increase or decrease the pressure within the gas chamber 22 to a level far beyond the typical changes due to breathing. Such an abrupt pressure change may lock the pressure switch 24 in either a closed or open position. Moreover, the gas chamber 22 must be in communication with ambient air pressure in order for the monitor 10a to function in changing weather conditions or at different altitudes with attendant changes in pressure. In accordance with this invention, the monitor 10 utilizes the orifice adapter 26 as a means of returning the pressure of the gas chamber 22 to ambient pressure. For the pressure switch 24 to function properly, it must be returned to its normal condition. In this embodiment, this normal condition is shown in solid lines in FIG. 3. This return to the normal condition must be within a relatively brief period (the pressure equalization time interval), typically no longer than about 5 seconds, but longer than the normal time it takes for the infant 20 to inhale and exhale.

The orifice adapter 26 has pressure equalization holes 28 in communication with ambient pressure. Alternately, an orifice adapter made of a porous material may be used. These holes 28 are of a size and number such that the pressure in the gas chamber 22 will return to the surrounding ambient pressure within about 5 seconds after a sudden pressure increase or decrease. The holes 28, however, are sufficiently restrictive so that changes in pressure within the gas chamber 22 due to the infant's motion are detected, causing the switch 24 to change states. With the pressure at ambient on both sides of the diaphragm 30, the contact 34 disengages from the contact 36, opening the switch 24. As discussed in greater detail in connection with the timing circuit 100, if the pressure switch 24 fails to open within a predetermined threshold period, the alarm 50 is activated.

The timing circuit 100 includes the audio alarm 50 such as, for example, a buzzer, an integrated circuit 42 purchased from Radio Shack and identified as Part No. 555 IC having pins 1 through 8 through which the integrated circuit 42 is connected to the contacts 34 and 36 of the switch 24 via a transistor Q1 having its emitter E connected to ground through the capacitor C1, its base B connected to one side of a manually actuated reset switch 53, the resistor R1, and the pin 2, and its collector C connected to the other side of the reset switch 53. The circuit 100 is powered by a nine volt power source 44, such as a battery or AC adapter, and a light emitting diode (LED) 46 displayed on the enclosures 14 and 14b indicates that power is available and monitoring is active. The reset switch 53 is mounted on the enclosures 14 and 14b.

The closure of the pressure switch 24 completes the timing circuit 100 to initialize a countdown timer (not shown) in the integrated circuit 42. The countdown timer threshold period, adjusted using a variable resistor R2, is nominally twenty seconds. As long as the infant 20 breathes normally, exhaling and inhaling within the threshold period, the cycling of the switch 24 between an open and closed state reinitializes the countdown timer. If the infant's 20 breathing should stop for longer than the threshold period, the countdown timer will not be reinitialized by pressure switch 24 cycling between an open and closed state, and will activate the alarm 50. Once the alarm has been acted upon by the parents, or other guardian, checking the infant 20, the reset switch 53 is activated to reinitialize the timer in the integrated circuit 42.

A third embodiment of this invention, as shown in FIGS. 4 and 5, improves portability of the monitor 10. In this third embodiment, a battery powered transmitter 154 may be installed to the sensing belt 12, enabling cordless operation between the sensing belt 12 and the timing circuit 100. In this configuration, the flexible tube 16 is greatly reduced in length to enable mounting of the orifice adapter 26, pressure switch 24, and battery powered transmitter 154 on the sensing belt 12. The pressure increase in the gas chamber 22 closes the contacts 34 and 36 in pressure switch 24, as discussed above, which activates the battery powered transmitter 154 to generate a radio signal which is transmitted to a receiver 156 (FIG. 5) in the timing circuit 100. This completes the electrical circuit between terminals 58 and terminal 60, activating the countdown timer of the integrated circuit 42 and alarm 50 as described above if the infant fails to inhale and exhale within the threshold period of the countdown timer. An alternate circuit is possible where, if the switch 24 fails to open or close within the threshold period, only then is the transmitter 154 activated to transmit to the receiver 156 a signal which produces the alarm.

In operation, the belt 12, or mat 18, is in contact with the infant 20 to detect motion which is indicative of the infant's breathing. The inhalation of the infant 20, expanding his or her chest 20a, causes the pressure inside the gas chamber 22 to increase slightly, typically about 0.05 inch of water, causing the pressure switch 24 to close and complete the circuit 100 to initialize the countdown timer. If the switch 24 is not opened within twenty seconds, the nominal threshold period of the countdown timer, the alarm 50 is activated. If, however, the infant exhales within the threshold period, and the switch 24 is opened, the countdown timer is reinitialized to prevent the alarm 50 from going off. If the infant 20, turns to cause an abrupt increase or decrease in the pressure within the pressure chamber 22, the pressure equalization holes 28 in the orifice adapter 26 return the pressure within the chamber 22 to ambient within the threshold period, thereby avoiding a false alarm. If the alarm goes off, and upon checking, the infant 20 is breathing normally, or the danger removed, the reset switch 53 is activated to reset the timing circuit 100.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

I claim:
1. A respiration monitor, including
   an alarm mechanism,
   a sensing element including a pressure chamber filled with gas, said sensing element being adapted to be placed in contact with a breathing subject, with the pressure in the chamber increasing as the subject inhales and decreasing as the subject exhales in accordance with a normal cycle of inhalation and exhalation,
   a pressure switch in communication with the pressure chamber, said switch changing from a first state to a second state as the subject exhales and changing from the second state to the first state as the subject inhales, and a timing circuit connected to the switch and including the alarm mechanism, said timing circuit activating the alarm mechanism when the switch fails to change from the second state to the first state within a predetermined threshold period, said chamber having at least one gas port which places the chamber in communication with ambient air pressure, so that within a pressure equalization time interval the pressure within the chamber equalizes to that of ambient air pressure and the switch changes from the second state to the first state, said port being sized so that said pressure equalization time interval is longer than the normal cycle of inhalation and exhalation of the subject but shorter than said predetermined threshold period and being sufficiently restrictive so that changes in pressure within the gas chamber are detected to cause the switch to change states.

2. The respiration monitor of claim 1 where said pressure switch is a differential pressure switch including a membrane with a first side of the membrane in communication with the gas chamber and a second side of the membrane in communication with ambient pressure.

3. The respiration monitor of claim 2 where the gas chamber has a predetermined total volume and the side of pressure switch in communication with the gas chamber has a small volume relative to the total volume of the gas chamber.

4. The respiration monitor of claim 1 where said alarm mechanism is an audio alarm.

5. The respiration monitor of claim 1 where said timing circuit includes a manually operated reset switch that resets the timing circuit after an alarm occurs.

6. The respiration monitor of claim 1 where said pressure equalization time interval is greater than 5 seconds and said predetermined threshold period is less than 25 seconds.

7. The respiration monitor of claim 1 where timing circuit includes a transmitter and a receiver in communication with transmitter, said transmitter sending a signal to the receiver to activate the alarm mechanism when the switch fails to change from the second state to the first state within said pressure equalization time interval.

8. The respiration monitor of claim 3 where at least 90 percent of the total volume of the gas chamber is located in the sensing element.

9. A respiration monitor, including an audio alarm mechanism, a sensing element made of a resilient material, said sensing element including a pressure chamber filled with gas, said sensing element being adapted to be placed in contact with a breathing subject, with the pressure in the chamber increasing as the subject inhales and decreasing as the subject exhales, a differential pressure switch in communication with the pressure chamber, with a first side in communication with the gas chamber and a second side in communication with ambient pressure, said switch changing from a first state to a second state as the subject exhales and changing from the second state to the first state as the subject inhales, said side of pressure switch in communication with the gas chamber having a volume small enough relative to the total volume of the pressure chamber that the change in volume due to the subject's inhalation and exhalation causes the switch to change states, and a timing circuit connected to the switch and including the alarm mechanism, said timing circuit activating the alarm mechanism when the switch fails to change from the second state to the first state within a predetermined threshold period, said chamber having at least one gas port which places the chamber in communication with ambient air pressure, so that within a pressure equalization time interval the pressure within the chamber equalizes to that of ambient air pressure and the switch changes from the second state to the first state, said port being sized so that said pressure equalization time interval is longer than the normal cycle of inhalation and exhalation of the subject but shorter than said predetermined threshold period and being sufficiently restrictive so that changes in pressure within the gas chamber are detected to cause the switch to change states.

10. The respiration monitor of claim 9 where said pressure equalization time interval is greater than 5 seconds and said predetermined threshold period is less than 25 seconds.

11. A method for detecting an onset of apnea in a subject breathing in accordance with a normal cycle of inhalation and exhalation, including placing the subject in contact with a sensing element having a pressure chamber filled with gas, said sensing element being adapted to be placed in contact with a breathing subject, with the pressure in the chamber increasing as the subject inhales and decreasing as the subject exhales, placing a differential pressure switch in communication with the pressure chamber, said switch changing from a first state to a second state as the subject exhales and changing from the second state to the first state as the subject inhales, and connecting to the switch a timing circuit including an alarm mechanism, said timing circuit activating the alarm mechanism when the switch fails to change from a second state to a first state within a predetermined threshold period, said chamber having at least one gas port which places the chamber in communication with ambient air pressure, so that within a pressure equalization time interval the pressure within the chamber equalizes to that of ambient air pressure and the switch changes from the second state to the first state, said port being sized so that said pressure equalization time interval is longer than the normal cycle of inhalation and exhalation of the subject but shorter than said predetermined threshold period and being sufficiently restrictive so that changes in pressure within the chamber are detected to cause the switch to change states.

12. A device for monitoring the respiration of a subject, comprising means for providing an alarm, means for sensing pneumatically the subject's breathing cycle by detecting inhalation and exhalation of said subject through deformation of an elastomeric gas chamber in physical contact with said subject, said sensing means providing an increase in pneumatic pressure as the subject inhales and a decrease in pneumatic pressure as the subject exhales, means for operating an electrical switch to change the state of the switch in response to the pressure changes provided by the sensing means, means for activating said alarm when the switch fails to change states within a predetermined threshold period, and means for equalizing the pneumatic pressure in said sensing means with ambient pressure within a pressure equalization time interval which is greater than said breathing cycle and shorter than said predetermined threshold period.

13. The device of claim 12 where said pressure equalizing means achieves ambient pressure in the sensing means in about 5 seconds.

14. The device of claim 12 where said means for operating an electrical switch utilizes a wireless means for changing the state of the switch.

* * * * *